United States Patent [19]
Schreiner

[11] Patent Number: 5,930,875
[45] Date of Patent: Aug. 3, 1999

[54] RETRACTABLE HOOK AND LOOP FASTENERS

[75] Inventor: David N. Schreiner, Quebec, Canada

[73] Assignee: Med-I-Pant Inc., Anjou, Canada

[21] Appl. No.: 08/925,312

[22] Filed: Sep. 8, 1997

[51] Int. Cl.$^6$ .................................................. A44B 18/00
[52] U.S. Cl. ............................................ 24/442; 604/391
[58] Field of Search ........................... 24/306, 442–452; 2/197; 267/74; 604/391

[56] References Cited

U.S. PATENT DOCUMENTS

| | | | |
|---|---|---|---|
| 838,486 | 12/1906 | Wildgen | 24/685 |
| 1,594,962 | 8/1926 | Jacobs | 267/74 |
| 4,011,600 | 3/1977 | Malk | 2/197 X |
| 4,537,591 | 8/1985 | Coates | 604/391 |
| 4,937,887 | 7/1990 | Schreiner | 2/402 |

*Primary Examiner*—James R. Brittain
*Attorney, Agent, or Firm*—McFadden, Fincham

[57] ABSTRACT

A retractable hook and loop fastener including a pocket of opposing substantially flat surfaces closed on opposite side edges and a rear edge, and having a front opening, an insert retractably secured within the pocket including a hook fastener portion, a tab arranged to extend beyond the front opening of the pocket and a slot through the insert having a rear end and a front end, an elastic anchor connecting the insert to the rear edge of the pocket, and a connector, such as a bar tack or rivet, joining points on opposite surfaces of the pocket through the slot. The arrangement of the present invention provides a fastener which reliably protects the hook portion from gathering lint or snagging other items during laundering or handling. The bar tack and slot serve to guide the travel of the insert in a relatively straight path without travelling too far out of the pocket or too far into the pocket, and eliminating problems with the insert twisting or folding inside the pocket.

18 Claims, 2 Drawing Sheets

RETRACTABLE HOOK AND LOOP FASTENERS

FIELD OF THE INVENTION

The present invention relates to hook and loop fasteners for garments and other laundered piece goods, particularly to an automatically retractable hook and loop fastener.

BACKGROUND OF THE INVENTION

Hook and loop fasteners, such as those marketed under the trade mark VELCRO™ and equivalents, provide desirable ease and flexibility of fastening for garments, coverings and other items. However, for items which require laundering, hook and loop fasteners present added difficulties. The hook portions tend to adhere to other items in the laundry often causing damage or wear. The hook portions also tend to attract and become clogged with lint, eventually becoming unusable. Exposed hook fasteners also cause difficulty for handling and sorting items which can easily become hooked together, snagged or damaged.

To prevent these problems time must be spent joining the hook portion to the loop portion before laundering. This is time consuming and costly in a commercial laundry. Also, garments, such as diapers, are less easily cleaned in the fastened arrangement.

Various solutions to prevent the hook portions of fasteners from being exposed during laundering and handling have been proposed. In U.S. Pat. No. 4,537,591 issued to Fredrica V. Coates, a fastener is disclosed which includes a cover comprising an additional loop portion joined to the hook portion in face to face arrangement. The two pieces are stitched together so that they are biased towards each other and tend to self close when the hook portion is not in use. This system is not completely satisfactory since some pressure is required on the hook and loop elements for positive closure. Repeated washing tends to soften and change the shape of the fastener resulting in misalignment, and the possibility of the hook portion catching a portion of the garment instead of the loop cover portion.

In a previous U.S. Pat. No. 4,937,887 issued to the present inventor, a fastener is disclosed having a pocket of semi-rigid material containing a hook portion retractably secured by an elastic ligament. In use the hook portion is drawn from the pocket to expose the fastening surface. Once released, the hook portion is retracted back into the pocket where it is completely covered for laundering and handling.

This system has proven to have a number of problems. The use of semirigid material helps to maintain the desired shape of the pocket, but it is expensive to manufacture and insert on garments. The fastener of this prior art design also proved ineffective as the dimensions of the desired hook tab were changed. For some applications a larger Velcro area is needed for good adhesion. However as the Velcro dimension is changed, most noticeably with a wide pocket, the flat shape of the fastener is not always maintained. The pocket can open allowing the hook insert to become twisted or folded inside. If the shape of the pocket is not maintained, the hook insert does not reliably retract. The hook portion may become curled or folded and more difficult to fasten. Further, the insert of the prior art design does not always extend and retract along a straight path, and therefore does not reliably retract to protect the hook portion of the fastener. The prior art design does not provide any means to maintain the pocket shape, or to guide the direction the insert travels.

Additional problems with the prior art design were found when the insert is able to retract too far and become folded inside the pocket. The insert is then difficult to retrieve and sometimes becomes hooked to the fibers of the elastic causing damage. After repeated washing the elastic of the fastener relaxes permitting the hook portion to be withdrawn farther from the pocket. If the hook portion of the insert is completely withdrawn from the pocket, the projecting hooks at the edge of the hook portion catch on the open edge of the pocket and the insert resists retracting smoothly. The prior art design provides no means to control the length of travel of the insert into and out of the pocket.

While automatic retraction still seems to be an attractive way to protect the hook portion of the fastener during laundering, a more reliable fastener design is clearly needed, particularly for use with commercially laundered items such as in hospitals or other institutions.

It is an object of the present invention to provide a retractable hook and loop fastener which protects the hook portion from gathering lint or snagging other items during laundering or handling.

SUMMARY OF THE INVENTION

Accordingly, the present invention comprises a retractable fastener, comprising:

a pocket of opposing substantially flat surfaces closed on opposite side edges and a rear edge, and having a front opening;

an insert retractably secured within the pocket including a hook fastener portion, the insert comprising a flexible web, which conveniently is stiffened with a layer of flexible PVC or the like, with at least a substantial portion of at least one face of the web forming or being covered with a hook fastener material;

means for retractably securing the insert inside the pocket;

a guide means cooperating between the insert and at least one surface of the pocket for defining a path of movement of the insert along at least one surface of the pocket and having a front stop means and a rear stop means; and a loop fastener portion associated with the hook portion for releasably engaging therewith.

In a further embodiment, the invention comprises a garment, comprising:
 a fabric portion;
 a hook fastener, including:
  a pocket of opposing substantially flat surfaces closed on opposite side edges and a rear edge, and having a front opening;
  an insert retractably secured within the pocket including a hook fastener portion, the insert being as characterized above;
  means for retractably securing the insert inside the pocket;
  a guide means cooperating between the insert and at least one surface of the pocket for defining a path of movement of the insert from a first position to a second position along the at least one surface of the pocket having a front end and a rear end; and
  a cooperating loop fastener for engaging the hook fastener.

A still further embodiment of the invention comprises a retractable hook fastener for use in cooperation with a compatible engaging surface, comprising:

a pocket of opposing substantially flat surfaces closed on opposite side edges and a rear edge, and having a front opening;

an insert retractably secured within the pocket including a hook fastener portion, a tab arranged to extend beyond the front opening of the pocket and a slot through the insert having a rear end and a front end;

an elastic anchor connecting the insert to the rear edge of the pocket; and a connecting means joining points on opposite surfaces of the pocket through the slot;

whereby the hook portion of the insert can be withdrawn from the pocket until the connecting means abuts the rear end of the aperture, when released the elastic anchor draws the hook portion into the pocket until the connecting means abuts the front end of the aperture. The insert is of the type characterized above, comprising a flexible web, one face of which forms a hook fastener.

The fastener according to the present invention may be constructed integrally with the garment or item, with the pocket fitted between inner and outer layers of the garment. Alternatively the pocket and insert may be manufactured as a separate unit and attached to the garment or item after its manufacture.

It is an advantage of the present invention to provide a fastener which provides reliable retraction and controlled movement by the centering and guiding functions provided by the connecting means.

It is a further advantage that the fastener of the present invention provides the comfort, flexibility and improved fit of an elastic fastening.

As a further advantage over the prior art, the present design is not as tolerance sensitive, allowing easier construction and more economic use of materials, since dimensional errors which might cause the insert to be over extended or retracted too far are prevented by the connecting means.

BRIEF DESCRIPTION OF THE FIGURES

Further details will be understood from the following drawings illustrating an embodiment of the invention by way of example only. Like numeral are used throughout to depict like elements.

DETAILED DESCRIPTION OF THE PREFERRED EMBODIMENTS

Figure 1:
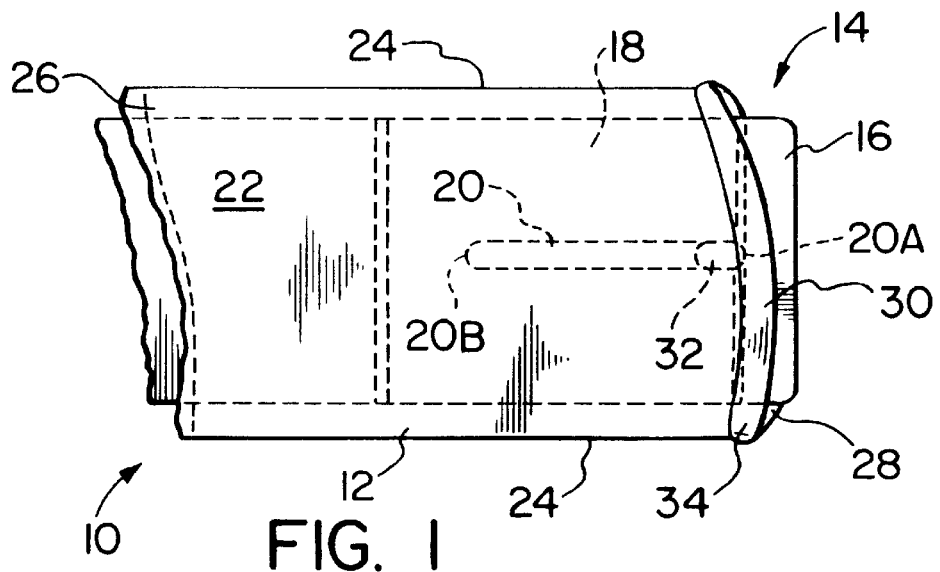
FIG. 1 shows a fastener according to the present invention, in a retracted position.
Figure 2:
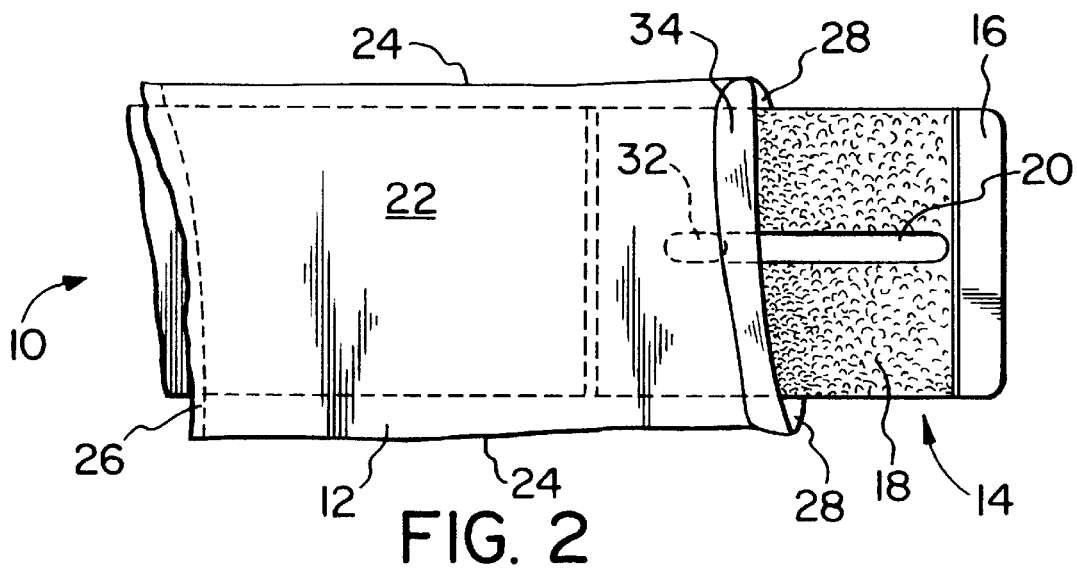
FIG. 2 shows the fastener of FIG. 1, in an extended position.

Referring to FIGS. 1 and 2, a fastener shown generally at 10, includes a pocket 12 and a retractable insert 14. The insert 14 is made up of a projecting tab 16, and a hook surface 18 including a guiding aperture 20 therein. An elastic anchor 22 secures the insert 14 to the rear edge 26 of the pocket. Two opposite side edges 24 and the rear edge 26 of the pocket 12 are sewn or appropriately sealed together. The opposing internal surfaces 28 of the pocket 12 are secured together near the open end 30 by a bar tack 32 through the aperture 20.

Preferably the insert 14 comprises a length of stiffening material to which a portion of hook material 18 is stitched or adhered on one side. An end of the stiffening material is allowed to project from pocket as a pull tab 16. The elastic anchor 22 is secured to the rear edge of the stiffening material or hook material 18 and at its opposite end into the seam of the rear edge 26 of the pocket 12. Preferably a stiffening layer is provided with a surface selected to reduce friction with the adjacent surface of the pocket 28. In a vinyl pocket, a stiffening layer of flexible PVC is preferred. It is necessary for the hook material to have a surface large enough to provide a secure hold to the loop material (not shown) to which it must be fastened for the specific purpose, and sufficient length for the rear edge to remain within the pocket 12 when the insert 14 is fully extended. It is desired to minimize the amount of hook material used in the fastener 10, as it is quite expensive.

Figure 3:
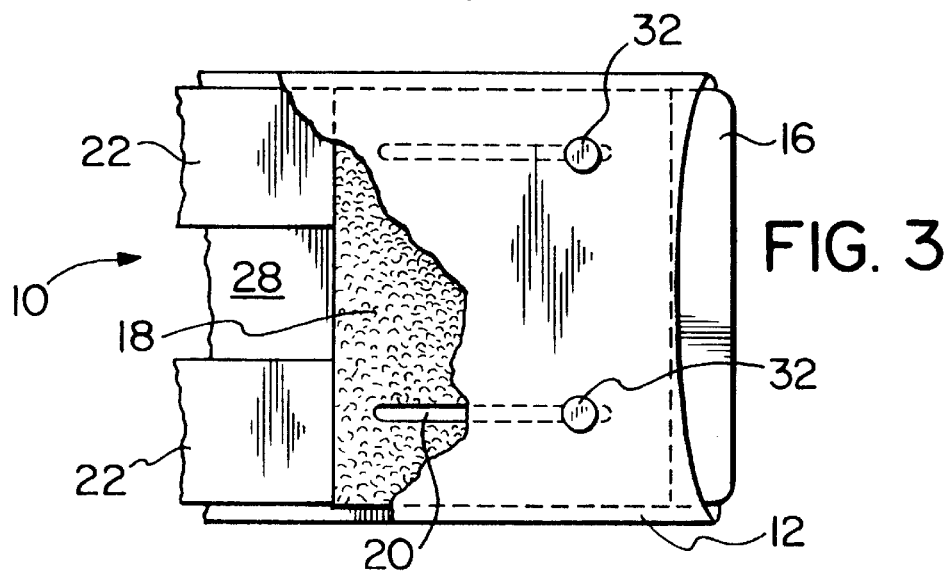
FIG. 3 shows a different embodiment of the fastener according to the present invention, with a portion of the pocket cut away for greater clarity.

The aperture 20 in the insert 14 is preferably in an elongated rounded shape. The front and rear ends 20A, 20B, of the aperture 20 form stops against which the bar tack 32 abuts at the ends of the insert travel. In this way the insert 14 is prevented from travelling too far into or out of the pocket 12. A relatively narrow elongated shaped slot provides the most control over the travel of the insert 14, preventing excess twisting or misalignment. The aperture 20 is most conveniently formed by a die cut. Advantageously the edges may be reinforced with stitching or heat sealing for strength an smoother operation. For particularly wide fasteners or greater control two or more apertures with corresponding bar tacks are used, as shown in FIG. 3.

The bar tack 32 (reinforced stitching), or other suitable connection means such as a rivet, button etc. joins the opposite surfaces 28 of the pocket 12 through the aperture 20 of the insert 14 keeping the pocket 12 relatively flat with the open end closed. Depending on the thickness of the insert 14, it may be desired to use a rivet or similar connection means which has a central shaft to maintain a space between the pocket surfaces. The bar tack 32 or connection means passes through the aperture 20, also serving to maintain the insert 14 in position and guide its travel along the aperture 20 straight into and out of the pocket 12. While the pocket 12 is held closed and flat, the insert 14 is prevented from folding or twisting inside.

At least one surface 28 of the pocket 12 should be of a smooth non-catching barrier material against which the hook material 18 can slide. Some suitable materials include vinyl fabric, nylon, coated fabric, PVC, etc. It is also preferred to place all stitching outside the pocket 12 where it cannot be snagged by the hook material 18. Particularly, the opening 30 of the pocket 12 is finished with a smooth binding 34 with the stitching located away from the protruding hooks. This can be accomplished by reverse stitching the binding 34 to an outer cover layer. Generally, only one surface of hook material 18 is required. Of course both surfaces of the insert 14 may carry hook material 18 for situations where two connections are required at the same point. In such a case, both surfaces of the pocket 12 should be formed of barrier material.

Figure 4:
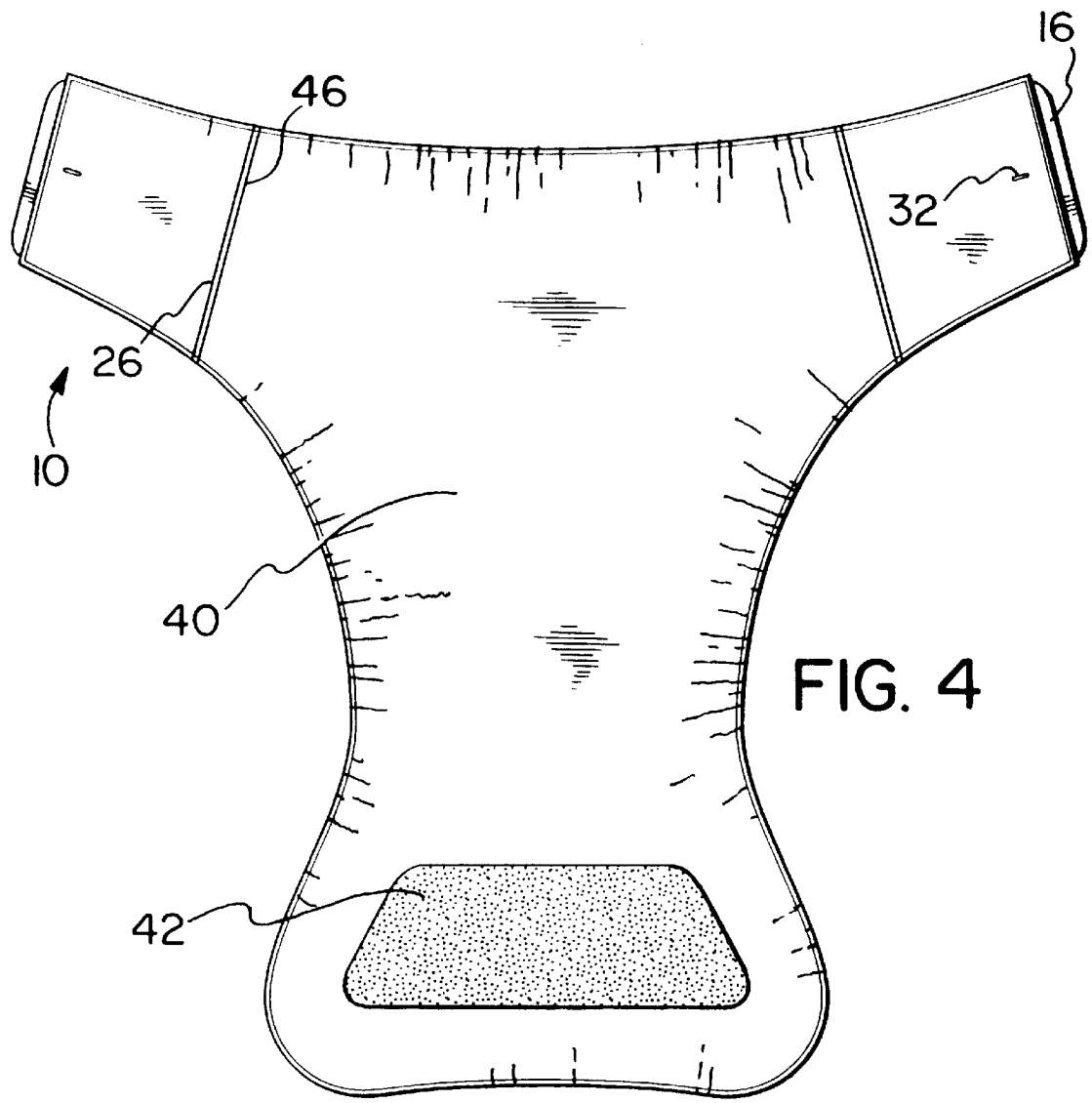
FIG. 4 shows a fastener according to the present invention attached to a diaper garment.

As seen in FIG. 4, the fastener 10 of the present invention can be sewn as a unit to be incorporated into commercial production. In this instance, the fastener 10 is sewn on to opposite corners of a diaper garment 40 to cooperate with a loop material 42 at the front of the garment 40. Particularly in this use the elastic property of the fastener 10 provides a more comfortable fit. The fastener may similarly be attached to a corner of a bib to close a neck opening, to other garments, to the corner of sheets or seat coverings to secure the same in place, and many other uses where it is desired to releasably secure flexible elements.

The fastener 10 is constructed by first assembling the insert 14. The tab 16, hook material 18, and elastic anchor 22 are assembled in line by stitching or equivalent method on a stiffening reinforcement layer if desired. The aperture 20 is cut. The insert 14 is then placed between the pocket surfaces 28, with the tab 16 correctly aligned. A smooth binding 34 may already be provided on the open edge 30 of the pocket elements. The pocket 12 is formed by stitching the three edges 24, 26 around the insert 14 and simultaneously tacking in the elastic anchor 22 in the rear edge 26. The bar tack 32 stitching, or rivet or other connection means is then placed between the two pocket surfaces 28 through the aperture 20. The pocket 12 may be inserted between two layers of the garment the fastener 10 is fitted to, or may comprise the layers of the garment, the pocket 12 being demarcated by the stitching around the insert 14. Alternatively the fastener 10 may be assembled as an individual unit to be attached to a surface or an edge of a finished garment.

In use the tab 16 is grasped to withdraw the insert 14 from the pocket 12 exposing the hook material 18 to be joined with a cooperating loop portion on the garment or where ever the fastener 10 is to be secured. The bar tack 32 guides the travel of the insert 14 against the aperture 20 in a relatively straight path out of the pocket 12 and stops the insert 14 from being drawn out too far. When the hook portion 18 is released from the loop portion, the elastic 22 automatically draws the insert 14 into the pocket 12. The bar tack 32 again guides the insert 14 on a relatively straight path into the pocket 12 and prevents it from being drawn in too far.

Figure 5:
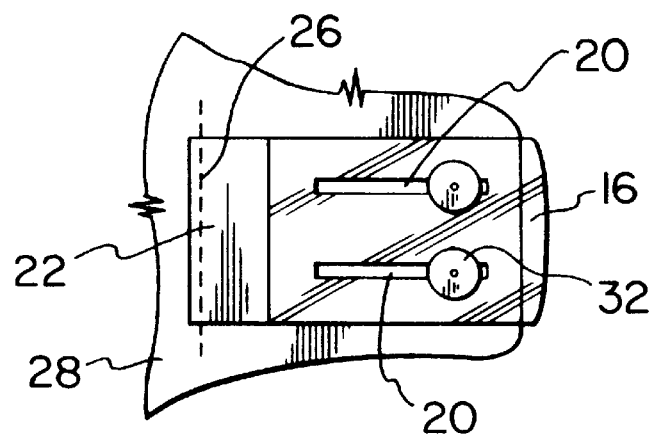
FIG. 5 illustrates an alternative embodiment of the present invention in which the outer surface of the pocket has been eliminated.

The covered appearance of the pocket is preferred for most uses, providing a smoother garment. However, the purpose of the present invention is to retract the hook portion of a fastener until it is covered by a smooth material. In situations where the fastener 10 is not visible during use of the article it is possible to dispense with the outer covering of the pocket 12 which does not face a hook surface, as shown in FIG. 5. The use of one or more buttons or rivets 50 through the apertures 20, having heads broader than the aperture in the insert 14 are sufficient to maintain the hook portion 18 of the insert 14 in sliding contact with the smooth covering 28. In all other ways the fastener 10 is the same.

Numerous other alternatives will be apparent to those of skill in the art. The previous embodiments are described as examples only, and are not to be interpreted as limiting the scope of the invention as defined in the appended claims.

I claim:

1. A retractable hook and loop type fastener, comprising:
   a pocket of opposing substantially flat surfaces closed on opposite side edges and a rear edge, and having a front opening;
   an insert retractably secured within the pocket said insert comprising a flexible web, one face of which is at least partly covered with hook fastener web means for retractably securing the insert inside the pocket;
   a guide means cooperating between the insert and at least one surface of the pocket for defining a path of movement of the insert along at least one surface of the pocket and having a front stop means and a rear stop means; and
   a loop fastener portion associated with the hook portion for releasably engaging therewith.

2. A retractable fastener as defined in claim 1, wherein the guide means comprises an aperture through the insert having a rear end and a front end, and a means within the aperture secured to the pocket.

3. A retractable fastener as defined in claim 2, wherein the aperture is a slot extending in the direction of movement between said first and second positions.

4. A retractable fastener as defined in claim 3, wherein the means within the aperture comprises a connecting means joining points on opposite surfaces of the pocket through the aperture and maintaining the opposing surfaces in a spaced apart configuration.

5. A retractable fastener as defined in claim 4, wherein the means for retractably securing the insert inside the pocket comprises an elastic anchor for securing the insert to the rear edge of the pocket.

6. A retractable hook fastener as defined in claim 5, wherein the fastener includes at least one connecting means and at least one cooperating aperture.

7. A retractable hook fastener as defined in claim 5, wherein the connecting means is mounted near the front opening.

8. A retractable hook fastener as defined in claim 5, wherein the connecting means is mounted at the front opening.

9. A retractable hook fastener as defined in claim 5, wherein the connection means comprises bar tack stitching.

10. A retractable hook fastener as defined in claim 5, wherein the connection means comprises a rivet.

11. A retractable hook fastener as defined in claim 5, wherein the elastic anchor has the same width as the hook fastener portion.

12. A retractable hook fastener as defined in claim 5, wherein at least one surface of the pocket comprises a barrier material.

13. A retractable hook fastener as defined in claim 5, wherein the insert further includes a reinforcing layer.

14. A retractable hook fastener as defined in claim 13, wherein the reinforcing layer has a surface compatible with the adjacent pocket surface to reduce friction.

15. A retractable hook fastener as defined in claim 5, wherein the insert further includes a tab arranged to extend beyond the front opening of the pocket.

16. A retractable hook fastener as defined in claim 2, wherein the pocket comprises a single surface against which the insert is slidably retained by an elastic anchor and the guide means comprises a button secured to the pocket surface through the aperture.

17. A garment comprising:
   a fabric portion;
   a hook fastener, including:
      pocket of opposing substantially flat surfaces closed on opposite side edges and a rear edge, and having a front opening;
      an insert retractably secured within the pocket, said insert comprising a flexible web, one face of which is at least partly covered with a hook fastener web;
      means for retractably securing the insert inside the pocket;
      a guide means cooperating between the insert and at least one surface of the pocket for defining a path of movement of the insert from a first portion to a second position along the at least one surface of the pocket and having a front stop means and a rear stop means a front end and a rear end; and
      a cooperating loop fastener for engaging the hook fastener.

18. A retractable hook fastener for use in cooperation with a compatible engaging surface, comprising:
   a pocket of opposing substantially flat surfaces closed on opposite side edges and a rear edge, and having a front opening;

an insert retractably secured within the pocket including a hook fastener portion, a tab arranged to extend beyond the front opening of the pocket and a slot through the insert having a rear end and a front end;

an elastic anchor connecting the insert to the rear edge of the pocket; and a connecting means joining points on opposite surfaces of the pocket through the slot;

whereby the hook portion of the insert can be withdrawn from the pocket until the connecting means abuts the rear end of the slot, when released the elastic anchor draws the hook portion into the pocket until the connecting means abuts the front end of the slot.

* * * * *